(12) United States Patent
Mori

(10) Patent No.: US 9,095,195 B2
(45) Date of Patent: Aug. 4, 2015

(54) CONTACT LENS CASE WITH LENS LOADING SURFACE

(75) Inventor: Osamu Mori, Kasugai (JP)

(73) Assignee: MENICON CO., LTD., Nagoya-shi (JP)

( * ) Notice: Subject to any disclaimer, the term of this patent is extended or adjusted under 35 U.S.C. 154(b) by 0 days.

(21) Appl. No.: 13/978,647

(22) PCT Filed: Feb. 14, 2011

(86) PCT No.: PCT/JP2011/000816
§ 371 (c)(1),
(2), (4) Date: Jul. 8, 2013

(87) PCT Pub. No.: WO2012/111038
PCT Pub. Date: Aug. 23, 2012

(65) Prior Publication Data
US 2013/0277242 A1    Oct. 24, 2013

(51) Int. Cl.
A45C 11/00    (2006.01)
(52) U.S. Cl.
CPC ..................... *A45C 11/005* (2013.01)
(58) Field of Classification Search
CPC ....................................................... A45C 11/005
USPC ............................................ 206/5.1; 134/901
See application file for complete search history.

(56) References Cited

U.S. PATENT DOCUMENTS

| | | | | |
|---|---|---|---|---|
| 4,543,882 | A * | 10/1985 | Ryder et al. | 206/5.1 |
| 5,474,169 | A * | 12/1995 | Bauman | 206/5.1 |
| 5,573,108 | A * | 11/1996 | Hamilton et al. | 206/5.1 |
| 5,711,416 | A * | 1/1998 | Bauman | 206/5.1 |
| 5,759,540 | A * | 6/1998 | Nielsen | 206/5.1 |
| 6,318,549 | B1 * | 11/2001 | Bougamont et al. | 206/5.1 |
| 7,086,526 | B2 * | 8/2006 | Newman | 206/5.1 |
| 7,410,050 | B2 * | 8/2008 | Py et al. | 206/5.1 |
| 7,461,740 | B2 * | 12/2008 | Newman | 206/5.1 |
| 7,828,137 | B2 * | 11/2010 | Newman | 206/5.1 |

(Continued)

FOREIGN PATENT DOCUMENTS

| | | |
|---|---|---|
| JP | A-04-022361 | 1/1992 |
| JP | A-05-269181 | 10/1993 |

(Continued)

OTHER PUBLICATIONS

Japan Patent Office Standard Technology Collection, General, Fiscal Year 2005, Glasses, p. 320 (technology name "13-2-2-1—Hydrogen Peroxide Method"), p. 323 (technology name "13-3-1-1 Liquid Storage Method").

(Continued)

*Primary Examiner* — Bryon Gehman
(74) *Attorney, Agent, or Firm* — Oliff PLC

(57) ABSTRACT

Provided is a contact lens case of a novel structure that will effectively supplement the sterilization effect which was insufficient in the past with non-heating type disinfectant methods such as the MPS method and hydrogen peroxide method, making it possible to realize an effective sterilization process on soft contact lenses. In a storage solution with a sterilizing action, a slanted loading member is provided, wherein a convex spherical lens loading surface is formed from an antimicrobial material and a contact lens is held in a slanted state such that a geometric center of the contact lens loaded on the lens loading surface is located at a position separated from a top of the lens loading surface.

8 Claims, 4 Drawing Sheets

(56) References Cited

U.S. PATENT DOCUMENTS

| | | | |
|---|---|---|---|
| 7,832,552 B2 * | 11/2010 | Newman | 206/5.1 |
| 7,850,002 B2 * | 12/2010 | Newman | 206/5.1 |
| 7,938,255 B2 * | 5/2011 | Newman | 206/5.1 |
| 8,596,782 B2 * | 12/2013 | Matsuzawa et al. | 206/5.1 |

FOREIGN PATENT DOCUMENTS

| | | |
|---|---|---|
| JP | A-05-341240 | 12/1993 |
| JP | A-06-205706 | 7/1994 |
| JP | Y-2541602 | 7/1997 |
| JP | A-10-313928 | 12/1998 |
| JP | A-2001-209015 | 8/2001 |
| JP | B2-3383083 | 3/2003 |
| JP | B2-4474057 | 6/2010 |
| WO | WO 2010/113208 A1 | 10/2010 |

OTHER PUBLICATIONS

National Consumer Affairs Center of Japan, issued Dec. 16, 2009, "Disinfecting Performance of Soft Contact Lens Disinfectant on *Acanthamoeba*," pp. 1-33.

May 17, 2011 International Search Report issued in Application No. PCT/JP2011/000816.

* cited by examiner

CONTACT LENS CASE WITH LENS LOADING SURFACE

TECHNICAL FIELD

The present invention relates to a contact lens case for holding soft contact lenses immersed in a storage solution having a sterilizing action.

BACKGROUND ART

When wearing soft type contact lenses repeatedly over a designated period such as several weeks or months, it is necessary to periodically implement a sterilization process on the contact lenses. This is to maintain a safe and comfortable wearing state by preventing eye infections and eye damage due to microorganisms such as bacteria, mold or the like.

However, though disinfection by boiling is known as one type of sterilization process for contact lenses, in the case of soft contact lenses, there are cases when degradation of the lens itself or thermal metamorphism of adhered substances become a problem. Furthermore, a special device is needed for the boiling disinfection process, and the work is troublesome, so a non-heating type disinfection method has been used for the soft contact lens sterilization process instead of boiling disinfection.

As this non-heating type disinfection method, typically known are an MPS method with which the contact lenses are stored in a disinfectant solution of polidronium chloride, and a hydrogen peroxide method with which the contact lenses are immersed in a hydrogen peroxide solution to neutralize them. For example, this is as noted on pages 320 and 323 of the Japan Patent Office Standard Technology Collection "Glasses" (Non-Patent Document 1).

However, even with these non-heating disinfection methods of the MPS method and the hydrogen peroxide method, it was still difficult to say that sufficient sterilizing action is exhibited on the soft contact lenses.

Specifically, with the former MPS method, to realize a simple operation that makes it possible to perform the washing, rinsing, disinfecting, and storage which constitute the care for soft contact lenses consistently using one solution for all of them, a solution that does not have a sufficient disinfecting or sterilizing action is used. Because of that, there is the problem that it was difficult to say sufficient sterilization effect is exhibited. This issue is also mentioned in for example the National Consumer Affairs Center of Japan paper, "Disinfection Performance of Soft Contact Lens Disinfectant on Acanthamoeba" (Non-Patent Document 2).

Meanwhile, with the latter hydrogen peroxide method, to avoid an adverse effect on the ocular tissue by hydrogen peroxide solution that has adhered to the contact lenses, simultaneous with the start of the sterilization process by immersing the contact lenses in hydrogen peroxide solution, the neutralization process is actively implemented using a catalyst or neutralizing solution. Because of that, by immersing the contact lenses in water after the hydrogen peroxide solution is neutralized, there was the risk that bacterial contamination would occur after neutralization.

BACKGROUND ART DOCUMENTS

Non-Patent Documents

Non-Patent Document 1: Japan Patent Office Standard Technology Collection, General, Fiscal Year 2005, Glasses, page 320 (technology name "13-2-2-1 Hydrogen Peroxide Method"), page 323 (technology name "13-3-1-1 Liquid Storage Method")

Non-Patent Document 2: National Consumer Affairs Center of Japan, issued Dec. 16, 2009, "Disinfecting Performance of Soft Contact Lens Disinfectant on Acanthamoeba"

SUMMARY OF THE INVENTION

Problem the Invention Attempts to Solve

The present invention was created with the circumstances described above as the background, and the problem it attempts to address is to provide a contact lens case of a novel structure that will effectively supplement the sterilization effect which was insufficient in the past with non-heating type disinfectant methods such as the MPS method and hydrogen peroxide method, making it possible to realize an effective sterilization process on soft contact lenses.

Means for Solving the Problem

A first mode of the present invention provides a contact lens case having a lens storage portion for storing a contact lens with the contact lens being immersed in a storage solution with a sterilizing action, and being configured to open upward, the contact lens case being characterized in that: a lens loading surface is provided projecting at a bottom part of the lens storage portion so as to have a spherical shape that is convex upward and be positioned under a liquid surface of the storage solution, while holding the contact lens in a state loaded with a spherical concave surface of the contact lens overlapping the lens loading surface, the lens loading surface is formed by an antimicrobial material, and a slanted loading member is provided for positioning a geometric center of the contact lens loaded on the lens loading surface at a position separated from a top of the lens loading surface.

With the contact lens case of this mode, in a state with the contact lens spherical concave surface loaded directly on the lens loading surface formed using an antimicrobial material, the contact lens is held in the lens storage portion immersed in storage solution. Therefore, in that held state, in addition to the sterilizing action of the storage solution, a sterilizing action by the antimicrobial material of the lens case is acting jointly on the contact lens spherical concave surface as well.

As a result, even in cases when the storage solution is an MPS solution, for example, the weak sterilizing action of the MPS solution is effectively supplemented by the sterilizing action of the lens case itself, and by the cooperating sterilizing action by both the solution and the lens case, it is possible to give an excellent sterilizing effect to the contact lens.

In particular, in a state with the contact lenses worn, the spherical convex surface is exposed to tear fluid which is actively made to flow with blinking and gravity action, so it is possible to inhibit adverse effects due to the adherence of microorganisms. On the other hand, the spherical concave surface is restricted in terms of tear exchange in a state substantially adhered to the cornea, so there is concern that there will be a great adverse effect due to adherence of microorganisms. Here, with the contact lens case of this mode, it is possible to actively have a sterilizing action by the lens case on the spherical concave surface of the contact lens, and it is possible to more effectively avoid adverse effects due to adherence of microorganisms.

In particular, with the contact lens case of this mode, by the geometric center of the contact lens being positioned separated from the top of the lens loading surface, the contact lens is loaded in a slanted state, so the lens edge (outer circumference edge part of the contact lens) is positioned facing opposite in the diametrical direction with the bottommost part at one end and the topmost part at other end. By doing this, even when air bubbles enter between contact lens loaded with the spherical concave surface facing downward and the lens loading surface, those air bubbles can easily be exhausted from the topmost part of the lens edge separated upward from the geometric center of the contact lens. As a result, the retention of air bubbles toward the bottom side of the contact lens is reduced, so it is possible to improve the adherence by more closely positioning the contact lens spherical concave surface and the lens loading surface, making it possible to exhibit the sterilizing action on the contact lens by the lens loading surface more effectively and stably.

As one contact lens case, a loading surface structural standalone unit that supports the contact lens spherical concave surface is disclosed in Japanese Patent No. 4474057, but this conventional structure contact lens case is in the first place not formed using an antimicrobial material, and makes no suggestion regarding the basic technical concept of "the sterilizing action of the non-heating type storage solution is supplemented by the sterilizing action of the contact lens case of antimicrobial material, so that excellent sterilizing action is realized," which is one of the features of this mode. Furthermore, there is nothing suggested regarding technology for promoting the exhausting of air bubbles which have entered the under side of the contact lens as described above. In addition to that, with the contact lens case of the conventional structure, in addition to the lens loading surface projecting to above the liquid surface, the contact lens is held in an extremely narrow area with the concave cap inner surface, so it is difficult to ensure a sufficient fluid volume for the storage solution with its sterilizing action to contact the contact lens. Also, even if the contact lens case of this conventional structure is formed with an antimicrobial material, many through holes are formed on the lens loading surface to have the storage solution contact the contact lens, so it is not possible to have the entire surface of the contact lens spherical concave surface loaded on the lens loading surface, and it is difficult to have sufficient contact surface area and thus to ensure antimicrobial action. In contrast to this, with this mode, by supporting the contact lens spherical concave surface in a loaded state and in a slanted state with the lens geometric center separated from the lens loading surface top by using the convex spherical lens loading surface provided under the liquid surface of the lens storage portion, it is possible to very effectively implement the sterilizing action by the contact lens case on the contact lens.

Furthermore, with the contact lens case of the present invention, the spherical concave surface of the contact lens is loaded overlapping the lens loading surface provided in a state projecting toward the opening part of the lens storage portion. Because of that, when either of the previously described disinfection methods of the MPS method and the hydrogen peroxide method are used, when the lens user takes the contact lens out after the sterilization process, it is possible to pick up the contact lens spherical convex surface with the fingers and place it on the rounded part of the fingertip, and to put the contact lens on the cornea as is. By doing this, it is possible to take the lens out from the lens storage portion and put it on the cornea without touching the fingers on the spherical concave surface of the contact lens for which it is particularly easy to have a problem of an adverse effect by bacterial contamination when wearing, and it is possible to more effectively exhibit the sterilizing effect on the spherical concave surface of the contact lens in a worn state.

The second mode of the present invention provides a contact lens case according to the first mode, wherein on a radial direction line extending opposite to a direction in which the geometric center of the contact lens separates from the top of the lens loading surface by means of the slanted loading member, a curvature radius of the lens loading surface is made smaller than a curvature radius of an inner surface of the contact lens so that a gap is formed between the lens loading surface and the inner surface of the contact lens at an outer circumference edge part of the contact lens.

With the contact lens case of this mode, by actively forming a gap between the contact lens inner surface and the lens loading surface on the topmost part side of the lens edge at which air bubbles that entered the under side of the contact lens can come out, the air bubbles can even more easily come out from the under side of the contact lens. In particular with this mode, by making the curvature radius of the lens loading surface smaller, it is possible to effectively form a gap for air bubbles to come out easily without having forced deformation of the contact lens.

The third mode of the present invention provides the contact lens case according to the first or second mode, wherein the slanted loading member is configured by having an outer circumference edge part of the lens loading surface be different on a circumference in a height direction so that a geometric center of the lens loading surface is set at a position separated from the top, and by a position of the outer circumference edge part of the contact lens being regulated by the outer circumference edge part of that lens loading surface so that the geometric center of the contact lens being positioned at a position separated from the top of the lens loading surface to a geometric center side of the lens loading surface.

With the contact lens case of this mode, by the lens loading surface itself being formed slanted from the vertical direction, it is possible to position the contact lens loaded on the lens loading surface with the geometric center at a position separated from the top in the vertical direction. Said another way, the bottom surface of the lens storage portion for which the lens loading surface is provided projecting is slanted, and the position of the contact lens on the lens loading surface is skewed, but this is limited by the abutment of the lens edge in relation to the slanted bottom surface on the outer circumference edge part of the lens loading surface, and the contact lens is held positioned in a slanted state.

The fourth mode of the present invention provides the contact lens case according to any one of the first through third modes, wherein on the lens loading surface, a groove part extending in a radial direction is formed with a side facing opposite a side for which the geometric center of the contact lens is separated from the top of the lens loading surface.

With the contact lens case of this mode, by a gap being actively formed between the inner surface of the contact lens and the lens loading surface using the groove part that extends in the direction to let out the air bubbles that entered the under side of the contact lens, it is even easier for the air bubbles to come out from the under side of the contact lens. It is possible to have just the suitable number of groove parts be provided, and also, to have them formed at least at the part at which the lens edge overlaps, and it is also possible to have the starting point of the center side of the lens loading surface with the groove part be the radial direction center part.

The fifth mode of the present invention provides the contact lens case according to any one of the first through fourth modes, wherein across an entire surface of an area on which the contact lens is loaded on the lens loading surface, a curvature radius of the lens loading surface is smaller than a curvature radius of the inner surface of the contact lens.

The contact lens case of this mode is able to avoid the situation in which only the outer circumference part of the contact lens spherical concave surface abuts the lens loading surface and the center part floats up from the lens loading surface. Because of that, the problem is avoided of it being difficult to remove air bubbles that have pooled at the center part of the contact lens which has floated up from the lens loading surface, and also, it is possible to exhibit the target sterilizing effect with even more stability by the center part of the inner surface of the contact lens being positioned sufficiently near the lens loading surface.

The sixth mode of the present invention is the contact lens case according to any one of the first through fifth modes, wherein hydrogen peroxide solution is held as the storage solution in the lens storage portion.

With the contact lens case of this mode, by using hydrogen peroxide solution as the storage solution, a very excellent sterilizing action is exhibited on the contact lens. On the other hand, in regards to the progression of bacterial contamination after neutralization which was a problem with the hydrogen peroxide method, by having the lens loading surface of the lens case formed using an antimicrobial material directly overlapped by the contact lens spherical concave surface, the sterilizing action of the lens case continues to act on the lens case, and it is possible to prevent progression of bacterial contamination. By doing this, the sterilizing action by the hydrogen peroxide solution and the sterilizing action by the lens case are exhibited with a mutually complementary relationship over time, and by the contact lens which initially was sufficiently sterilized by hydrogen peroxide solution having the sterilized state maintained by the lens case, it is possible for the lens user to safely wear contact lens in a sterilized state.

The seventh mode of the present invention provides the contact lens case according to the sixth mode, wherein a catalyst storage portion that holds a catalyst exhibiting a catalytic action on a decomposition reaction of the hydrogen peroxide solution is provided with a bottom surface thereof being located at a same or greater depth as a bottom surface of the lens storage portion, and a bottom part communication flow path is provided that causes communication between the lens storage portion and the catalyst storage portion at the bottom part.

With the contact lens case of the present invention, even if the bottom surface of the catalyst storage portion is shallower than the bottom surface of the lens storage portion, as long as both the catalyst and the contact lens are under the water surface, it is possible to exhibit an effective sterilizing effect. However, for example it is also possible to have the bottom surface of the catalyst storage portion have the same or greater depth as the bottom surface of the lens storage portion as in the case of this mode. Then, in a case when the bottom surface of the catalyst storage portion is the same or greater depth than the bottom surface of the lens storage portion as with this mode, the hydrogen peroxide solution which has a greater specific gravity than the water after decomposition is led from the lens loading surface through the bottom part communication flow path toward the catalyst storage portion. By doing this, along with the progression of neutralization of the hydrogen peroxide solution by the catalytic action in the catalyst storage portion, using the difference in specific gravity, the un-neutralized hydrogen peroxide solution is actively led from the lens loading surface toward the catalyst storage portion. As a result, the catalytic action by the catalyst held in the catalyst storage portion is also effectively implemented on the hydrogen peroxide solution held in the lens storage portion, and it is possible to efficiently manifest stable progression of uniform neutralization on all of the hydrogen peroxide solution held inside the case.

More preferably with this mode, to promote the flow of hydrogen peroxide solution in the hydrogen peroxide solution flow path containing the bottom part communication flow path, a bottom surface slanted downward or the like toward the bottom surface of the catalyst storage portion from the bottom surface of the lens storage portion is provided. Also, between the lens storage portion and the catalyst storage portion, in addition to the bottom part communication flow path, a liquid surface communication flow path that allows reciprocal communication is provided at the liquid surface area as well. By doing this, using the fluid flow generated by the oxygen gas that is generated in the perimeter of the catalyst in the catalyst storage portion and floats on the liquid surface then diffuses in the perimeter near the liquid surface, a fluid flow is actively generated in the liquid surface area from the catalyst storage portion toward the lens storage portion. Together with the fluid flow from the lens storage portion toward the catalyst storage portion in the bottom part, it is possible to more efficiently generate a fluid flow that has overall circulation between the lens storage portion and the catalyst storage portion.

Also, the eighth mode of the present invention provides the contact lens case according to the sixth or seventh mode, wherein the catalyst exhibiting a catalytic action on the decomposition reaction of the hydrogen peroxide solution is used, and the catalyst includes a catalyst main unit and a frame unit enclosing an outer circumference of the catalyst main unit.

With the contact lens case of this mode, by the catalyst using the frame unit that encloses the outer circumference of the catalyst main unit, it is possible to limit excess diffusion in the perimeter of the air bubbles generated by the decomposition action of the hydrogen peroxide solution. Because of that, it is also possible to suppress things like the air bubbles diffusing to the lens storage portion and entering the under side of the contact lens. For the frame unit of this mode, preferably used is an item having a tube shape extending in a vertical direction in the hydrogen peroxide solution, and more preferably is a shape for which the bottom edge part of the frame unit extends downward the same or more than the bottom edge part of the catalyst main unit. By doing this, it is possible to even more effectively inhibit the diffusion of air bubbles particularly generated near the bottom part of the hydrogen peroxide solution, and their entering to the under side of the contact lens.

Also, the ninth mode of the present invention provides the contact lens case according to any one of the first through eighth modes, wherein a lid unit that closes the lens storage portion is provided to be able to open and close, and a restricting projection that restricts floating up of the contact lens from the lens loading surface is provided on an inner surface of the lid unit so as to be positioned facing the lens loading surface of the lens storage portion and project as far as the storage solution.

With the contact lens case of this mode, it is possible to more stably exhibit the sterilizing effect of the lens loading surface on the spherical concave surface of the contact lens. Specifically, when a portion of the air bubbles remain on the under side of the contact lens, the contact lens floats up and a large gap occurs between the contact lens spherical concave surface and the lens loading surface, and there is the risk of it becoming difficult to sufficiently exhibit the target sterilizing effect by the lens loading surface. In particular, with the hydrogen peroxide method, there is the risk of the oxygen gas generated with the neutralization process entering to the under side of the contact lens. In light of that, with this mode, the contact lens is pressed down by the restricting projection, and it is possible to keep a state of being near or in contact with the lens loading surface. By doing this, it is possible to more stably obtain the sterilizing effect by the lens loading surface on the contact lens.

Effect of the Invention

With the contact lens case constituted according to the present invention, it is possible to have complementary exhibiting of both the sterilizing action of the storage solution and the sterilizing action by the antimicrobial material of the lens case on the contact lens held in the lens storage portion. As a result, for example with the MPS method, it is possible to obtain a comprehensive excellent sterilizing effect by the weak sterilizing action of the storage solution being supplemented by the sterilizing action of the lens case, and with the hydrogen peroxide method, it is possible to obtain a comprehensive excellent sterilizing effect by the sterilized state after decomposition being maintained with the sterilizing action of the lens case. In particular, on the contact lens spherical concave surface for which bacterial contamination easily becomes a problem with the low tear exchange efficiency in the worn state, by providing the lens loading surface directly overlapping, the sterilizing action by the antimicrobial material of the lens case can be more effectively exhibited for the problem of bacterial contamination that comes with wearing of contact lens.

In particular, with the contact lens case of the present invention, the contact lens is held in a slanted state on the lens loading surface, so even if air bubbles enter the under side of the contact lens, those air bubbles can be easily exhausted from the topmost part of the lens edge. Because of that, it is possible to improve the adherence with closer positioning of the contact lens spherical concave surface and the lens loading surface, and it is possible to more effectively have stable exhibition of the sterilizing action on the contact lens of the lens loading surface.

EMBODIMENTS FOR CARRYING OUT THE INVENTION

Figure 1:
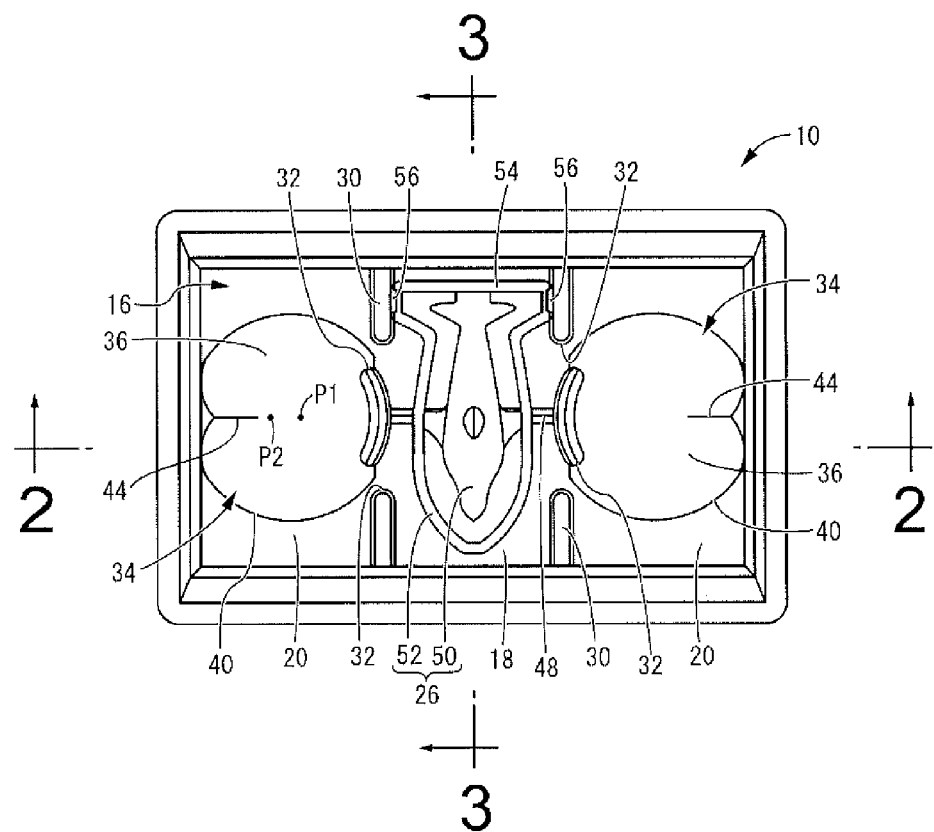
FIG. 1 is a plan view showing a case main unit of a contact lens case as a first embodiment of the present invention.

Following, we will describe embodiments of the present invention while referring to the drawings.

Figure 5:
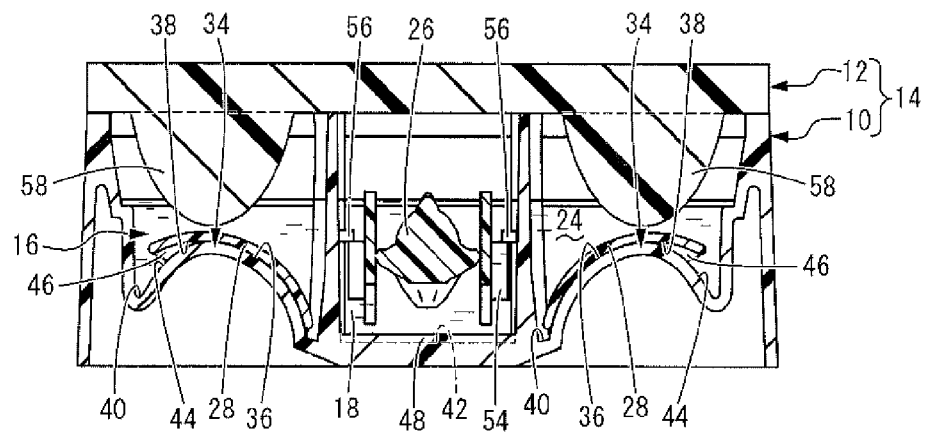
FIG. 5 is a cross section view showing an example in a used state of the overall structure of the contact lens case with a lid unit mounted on the case main unit shown in FIGS. 1 to 4.

A case main unit 10 is shown in FIG. 1 through FIG. 4, and as shown in FIG. 5, by mounting a lid unit 12 on this case main unit 10, this becomes the contact lens case 14 which is a first embodiment of the present invention. FIG. 5 shows the contact lens case 14 in a used state.

In more detail, the case main unit 10 has a roughly rectangular block shape overall, an opening is made in a rectangular shape on its top surface, and a liquid holding recess 16 is formed. This liquid holding recess 16 is constituted from a catalyst storage portion 18 positioned at the center part in the horizontal direction (horizontal in FIG. 1) and a pair of lens storage portions 20, 20 positioned at both side parts in the horizontal direction.

Then, as shown in FIG. 5, when doing sterilization processing, as the storage solution with a sterilizing action in the liquid holding recess 16, a 3% concentration of hydrogen peroxide solution 24 is held, and this hydrogen peroxide solution 24 can be stored in both of the catalyst storage portion 18 and the lens storage portions 20, 20.

Also, both the catalyst storage portion 18 and the lens storage portions 20, 20 are recesses that are opened on the top surface of the case main unit 10, and a catalyst 26 that exhibits a catalytic action on the neutralization reaction of the hydrogen peroxide solution is held in the catalyst storage portion 18. Meanwhile, soft type left and right contact lenses 28, 28 are respectively held in the lens storage portions 20, 20 (see FIG. 5).

Furthermore, partition walls 30 extending in the front-back (vertical in FIG. 1) direction are formed respectively at both the left and right sides of the catalyst storage portion 18, specifically, the boundary between the catalyst storage portion 18 and the lens storage portions 20, 20. This partition wall 30 projects out from the bottom surface of the liquid holding recess 16, and reaches roughly as far as the opening part of the liquid holding recess 16. Also, a suitable number (with this embodiment, two) of cutout windows 32 are formed in the front-back direction, and by having these cutout windows 32 be of a size that reaches from the base end part of the partition wall 30 to the tip end part, the constitution is such that the partition wall 30 is divided into a plurality in the front-back direction.

Then, the contact lenses 28, 28 held in the left and right lens storage portions 20, 20 are both made to be kept within the lens storage portion 20, 20 by these partition walls 30, 30. By doing this, the contact lenses 28, 28 held in the lens storage portions 20, 20 are prevented from moving to the catalyst storage portion 18 and contacting the catalyst 26.

Also, the left and right lens storage portions 20, 20 are connected to the catalyst storage portion 18 by the cutout windows 32 formed on each partition wall 30. By doing this, the pooled hydrogen peroxide solution 24 is made to be able to mutually flow through the cutout windows 32 as communication flow paths between the left and right lens storage portions 20, 20 and the catalyst storage portion 18. In particular with this embodiment, the cutout windows 32 have a depth that reaches each bottom part of the lens storage portions 20 and the catalyst storage portion 18. By doing that, the bottom part communication flow path that communicates between both bottom parts of the lens storage portion 20 and the catalyst storage portion 18 as well as the liquid surface communication flow path that communicates between both liquid surface parts are constituted by the cutout windows 32.

Furthermore, lens support parts 34, 34 that project facing upward which is the opening direction of the lens storage portion 20 are formed respectively on the center part of the bottom part of the left and right lens storage portions 20, 20. This lens support part 34 has a partial spherical shape for which a roughly constant curvature radius sphere is cut in a small circle, and is provided projecting upward from the roughly circular bottom surface of the lens storage portion 20. By doing this, a spherical shaped lens loading surface 36 is constituted by the surface of the lens support part 34. Also, the lens support part 34 is formed with a sufficiently lower height dimension (specifically, a maximum height dimension lower than the liquid surface height of the hydrogen peroxide solution 24) than the depth dimension of the lens storage portion 20 so that the overall lens loading surface 36, with the case main unit 10 in a state loaded flat on a horizontal support surface, is under the water surface of the hydrogen peroxide solution 24 in the lens storage portion 20.

A spherical concave surface 38 of the contact lens 28 is made to be supported by being overlapped on the lens loading surface 36. At that time, the lens loading surface 36 is preferably not provided with a hole or the like so that the lens loading surface 36 is positioned facing opposite across roughly the entire surface of the spherical concave surface 38 of the contact lens 28.

Also, it is desirable that the lens loading surface 36 be set to a curvature radius roughly approximating the curvature radius R1 of the contact lens spherical concave surface 38 so that the entire surface is overlapped sufficiently near the spherical concave surface 38 of the overlapped contact lens 28. Preferably, it is good to set the curvature radius of the lens loading surface 36 to within a range of R1±5 mm taking into consideration the flexibility of the curvature radius of contact lenses which have a high water content such as soft contact lenses. More preferably, the loading area of the contact lens 28 on the lens loading surface 36 has desirably a smaller curvature radius than the curvature radius of the spherical concave surface 38 of the contact lens across the entire surface. By doing that, between the facing surfaces of the spherical concave surface 38 of the contact lens 28 and the lens loading surface 36, the generation of a gap at the center part of the contact lens 28 is effectively prevented, and it is possible to avoid problems such as an increase in the distance between facing surfaces due to the gap, retention of air bubbles in that gap, and the like.

Furthermore, with this embodiment, by the lens support part 34 being provided projecting at the center part of the lens storage portion 20, a roughly ring shaped circumferential groove 40 for which the periphery of the lens support part 34 extends in the circumference direction is formed. Also, by having the peripheral wall inner surface of the lens storage portion 20 be a slanted surface that expands facing the opening part, having the slant angle facing that opening part or the slanted surface length differ in the circumference direction or the like, the depth of the circumferential groove 40 differs in the circumference direction. Specifically, a slope slanting downward toward the catalyst storage portion 18 is added on the circumferential groove 40 so that the depth dimension of the circumferential groove 40 becomes the deepest on the catalyst storage portion 18 side and the shallowest on the opposing case peripheral side.

Then, the circumferential groove 40 of the lens storage portion 20 is connected to a bottom surface 42 of the catalyst storage portion 18 through the cutout window 32 provided on the partition wall 30. Also, the bottom surface 42 of the catalyst storage portion 18 has a depth dimension that is the same or greater than that of the deepest part of the bottom surface of the lens storage portion 20, and in particular with this embodiment, at the area including the bottom surface of the formation part of the cutout windows 32, 32 that continue into the left and right lens storage portions 20, 20, a slope is added that gradually slants downward from the bottom surface of the lens storage portion 20 (bottom surface of the circumferential groove 40) toward the bottom surface 42 of the catalyst storage portion 18. By doing this, on the bottom surface of the liquid holding recess 16 of the case main unit 10, overall there is added a slope that slants gradually downward from both left and right end parts at which the lens storage portions 20, 20 are positioned toward the center part at which the catalyst storage portion 18 is provided.

Furthermore, by the bottom part of the circumferential groove 40 that constitutes the bottom surface of the lens storage portion 20 being a slanted surface that slants downward toward the catalyst storage portion 18 as described above, the lens support part 34 formed projecting out from there is tilting in the same direction overall. In other words, the lens loading surface 36 of the lens support part 34 has its geometric center (surface area center point with a front view in the direction orthogonal to the bottom surface of the lens storage portion 20) P1 set at a position separated downward at the catalyst storage portion 18 side from its top (highest point in the vertical direction in a state with the case main unit 10 placed flat) P2.

The lens loading surface 36 has an outer circumference shape that is larger than the contact lens 28 by a designated amount. The contact lens 28 overlapping the lens loading surface 36, by the outer circumference edge (lens edge) abutting the circumference wall of the lens storage portion 20 and the bottom surface of the circumferential groove 40, is held positioned at roughly the center of the lens loading surface 36. By doing this, the contact lens 28 has its geometric center (optical center when a spherical lens) separated to the geometric center P1 side from the top P2 of the lens loading surface 36, at roughly the same position as that geometric center P1, and the overall contact lens 28 is held slanted to the catalyst storage portion 18 side.

Also, with this embodiment, on the lens loading surface 36, a groove part 44 extending toward the center from the outer circumference edge part is formed on the radial direction line facing opposite P1 from the top P2. Specifically, this groove part 44 is provided on the upper side (upward of the slant direction of the bottom surface of the lens storage portion 20) opposite to the lower side (catalyst storage portion 18 side) at which the geometric center of the contact lens is separated from the top P2 of the lens loading surface 36. Then, by this groove part 44 being formed, the overall shape of the lens loading surface 36 is roughly a heart shape narrowed toward the catalyst storage portion 18 (see FIG. 4).

Figure 2:
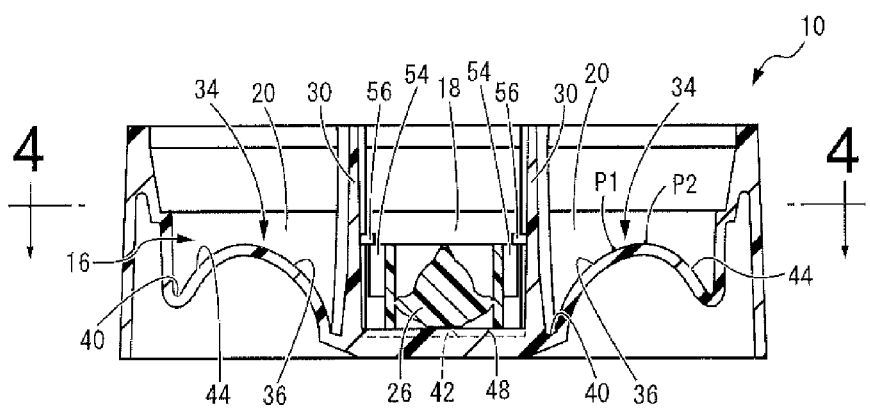
FIG. 2 is a cross section view of 2-2 in FIG. 1.
Figure 3:
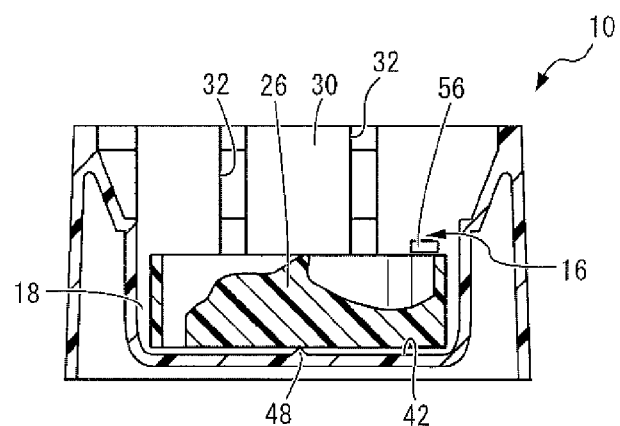
FIG. 3 is a cross section view of 3-3 in FIG. 1.
Figure 4:
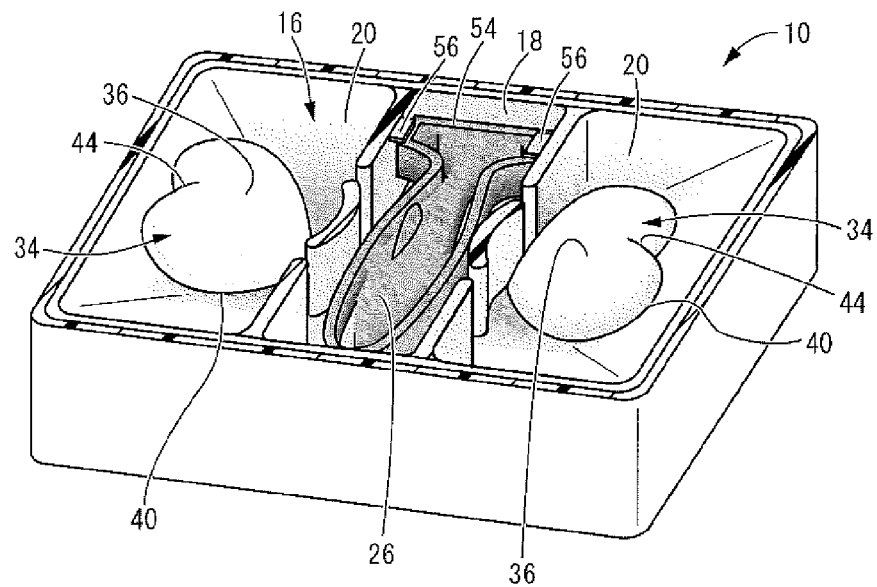
FIG. 4 is a perspective view of the case main unit shown in FIG. 1.

Furthermore, the upper side part on which the groove part 44 is formed on the lens loading surface 36 has a smaller curvature radius than the lower side part as shown in FIG. 2 and FIG. 5. By doing this, at the groove part 44 forming area, a gap 46 is actively formed between the lens loading surface 36 and the inner surface of the contact lens 28, and this gap 46 is opened outward from the outer circumference edge part of the contact lens 28.

Meanwhile, the catalyst 26 arranged held in the center catalyst storage portion 18 has at least a portion of the surface in contact with the hydrogen peroxide solution 24 formed by a material that exhibits a catalytic action in the decomposition of the hydrogen peroxide solution 24. Any known item can be used for this material, but it is preferable to use a metal catalyst so as to be able to exhibit a stable catalytic action when doing the contact lens sterilization process a plurality of times. To give specific examples, at least one type of a metal consisting of the group including platinum, silver, palladium, copper, manganese, cobalt, and aluminum, and metal oxides of these, is used as the material of the catalyst 26.

In particular with this embodiment, the mass, surface area, and shape of the catalyst 26 are suitably set and the buoyancy of the oxygen gas that acts on the catalyst 26 is adjusted. By so doing, during hydration of the hydrogen peroxide solution 24, while initially the catalyst 26 floats up to the water surface of the hydrogen peroxide solution 24, when hydration is complete, the catalyst 26 sinks in the hydrogen peroxide solution 24. In more detail, roughly the entire surface of the catalyst 26 which has a fish shape is covered by a metal catalyst, and while the surface area is made bigger by the concave parts and convex parts that form the fish, a projection in a dorsal fin shape is provided on the back surface of the fish shape, and by that projecting out above the water surface of the hydrogen peroxide solution 24 when floating up, it is possible to easily visually recognize the level at which the catalyst 26 has floated up. A support projection 48 which extends to left and right at the center is formed projecting on the bottom surface 42 of the catalyst storage portion 18. Then, by having the bottom surface of the catalyst 26 immersed in the hydrogen peroxide solution 24 ride on the tip of the support projection 48, the overall bottom surface of the catalyst 26 is prevented from adhering on the bottom surface 42 of the catalyst storage portion 18.

Also, a frame unit 52 that encloses across the entire circumference of the periphery of a catalyst main unit 50 which has a fish shape is provided as an integral unit on the catalyst 26. This frame unit 52 is a tube shape that encloses across the entire circumference of the periphery of the catalyst main unit 50 in the vertical plate cross section extending in the vertical direction. Also, the bottom edge of the frame unit 52 is roughly the same as the bottommost edge of the catalyst main unit 50, and the top edge of the frame unit 52 is roughly the same as the topmost edge of the catalyst main unit 50. In other words, the frame unit 52 is shaped with a shape and size that covers and hides the catalyst 26 with any side surface view across the entire circumference.

Furthermore, at one end part in the length direction of the catalyst 26 (the tail side end part of the fish shape), a support shaft part 54 projecting outward in the left and right direction is provided as an integral unit with the frame unit 52. Meanwhile, a pair of engaging pieces 56, 56 are provided facing in the left and right direction on the far side (upward in FIG. 1) in the catalyst storage portion 18 of the case main unit 10. Then, both end parts of the support shaft part 54 of the catalyst 26 are supported positioned to be able to rotate with floating up of the support shaft part 54 suppressed by engaging with the pair of engaging pieces 56, 56.

With the catalyst 26 supported by the support shaft part 54 in this way, by allowing rotation around the center shaft of the support shaft part 54 extending in the left and right direction, gradual changes in the level of the buoyancy due to oxygen gas accompanying the progression of neutralization of the hydrogen peroxide solution 24 cause rocking around the center shaft of the support shaft part 54. As a result, as described above, a sink-float operation is manifested by which the catalyst 26 floats up (the head side of the fish shape floats up) at the start of hydration of the hydrogen peroxide solution 24 and sinks at hydration completion.

However, with the case main unit 10 constituted as described above, at least the lens support part 34 constituting the lens loading surface 36 is formed using an antimicrobial material, and with this embodiment, the overall case main unit 10 is formed as an integral unit with an antimicrobial material.

As specific antimicrobial materials, known items can be suitably used, but for example as noted in Japanese Unexamined Patent Publication No. JP-A-4-22361, Japanese Utility Model Registration No. 2541602, Japanese Patent No. 3383083, Japanese Unexamined Patent Publication No. JP-A-2001-209015, Japanese Unexamined Patent Publication No. JP-A-5-269181, and Japanese Unexamined Patent Publication No. JP-A-5-341240, polymer compounds containing antimicrobial metals such as silver, copper, zinc and the like can be suitably used.

Then, by the lid unit 12 that can open and close being mounted on the top surface of this case main unit 10, the opening of the liquid holding recess 16 is covered across its entirety. This lid unit 12 is roughly a rectangular plate shape overall, and the outer circumference part of its bottom surface is a surface overlapping the opening circumference edge part of the liquid holding recess 16 of the case main unit 10. Meanwhile, at the center part of the lid unit 12, a pair of restricting projections 58, 58 are formed projecting positioned at both the left and right sides. These restricting projections 58, 58 are provided at positions facing the lens support parts 34, 34 when the lid unit 12 is mounted on the case main unit 10.

In particular with this embodiment, the restricting projections 58, 58 are provided projecting with a spherical convex surface the same as with the lens support parts 34, 34, and in a closed state with the lid unit 12 mounted on the case main unit 10, the tip peak parts of the restricting projections 58 and the lens support parts 34 are made to be positioned facing opposite each other across a designated gap in the vertical direction. Specifically, with the restricting projection 58 of the lid unit 12, in a state mounted on the case main unit 10, at least the tip part is at a height projecting downward from the water surface of the hydrogen peroxide solution 24 pooled in the case main unit 10. Also, in that state, the gap between the opposite facing peaks of the restricting projections 58 and the lens support parts 34 is slightly larger than the thickness dimension of the contact lens 28 held in the contact lens case 14.

By doing this, inside the contact lens case 14, floating up of the contact lens 28 held in the lens storage portion 20 and loaded on the lens loading surface 36 of the lens support part 34 is restricted by the restricting projection 58. As a result, the contact lens 28 is prevented from floating up to the water surface of the hydrogen peroxide solution 24, and is made to be kept submerged in the water of the hydrogen peroxide solution 24 and in a state loaded on the lens loading surface 36.

Using the contact lens case 14 constituted as described above, the contact lenses 28, 28 undergo sterilization processing as noted hereafter, for example. First, the contact lens user places the case main unit 10 for which the lid unit 12 has been removed in a flat state on a table or the like, and inserts and pools in the liquid holding recess 16 the hydrogen peroxide solution 24 for lens sterilization prepared in advance.

Furthermore, before or after insertion of the hydrogen peroxide solution 24 to the case main unit 10, the user removes the contact lenses 28, and holds the removed contact lenses 28 in the lens storage portion 20 of the case main unit 10. At that time, the contact lenses 28 are held in the lens storage portion 20 in a convex state facing upward, and the spherical concave surface of the contact lenses 28 is overlapped on the lens loading surface 36.

After that, by covering the lid unit 12 on the case main unit 10 and assembling, the sterilization process of the contact lenses 28, 28 is started. Specifically, by the contact lenses 28, 28 held in the lens storage portions 20, 20 being immersed in the hydrogen peroxide solution 24, the contact lenses 28, 28 are sterilized over a designated time. This sterilization process of the contact lenses 28, 28 by the hydrogen peroxide solution 24 continues until the decomposition reaction of the hydrogen peroxide solution 24 progresses and neutralization is roughly completed.

Oxygen gas is generated particularly in the perimeter of the catalyst 26 during the decomposition reaction of the hydrogen peroxide solution 24, but since the catalyst storage portion 18 is partitioned from the lens storage portions 20, 20 by the partition wall 30, movement of the generated oxygen gas to the lens storage portions 20, 20 is inhibited.

In fact, the contact lens 28 loaded on the lens loading surface 36 is held in a slanted state on the lens support part 34 by a slanted loading member constituted from one or a plurality of: a constitution that slants the overall lens loading surface 36; a biasing constitution of the geometric center P1 and the top P2 on the lens loading surface 36; a constitution abutting the contact lens 28 against the circumference wall of the lens storage portion 20 or the bottom surface 42 of the circumferential groove 40; or curvature radius distributions or the like set for each part of the lens loading surface 36. In particular, with this embodiment, in a state for which the outer circumference edge part (lens edge) of the contact lens 28 has the bottommost part at the catalyst storage portion 18 side, and has the topmost part on the diametrical direction opposite side, this is held positioned slanted in the left-right direction of the case main unit 10. Particularly preferably, it is desirable that the bottommost point of the contact lens 28 supported overlapping the lens loading surface 36 be positioned below the bottommost point of the catalyst 26 that floated up during neutralization of the hydrogen peroxide solution 24.

With the contact lens 28 held slanted in this way, of the outer circumference edge part (lens edge), the part positioned the furthest upward (each end part positioned at both the left and right sides of the case main unit 10 in FIG. 5), the opening angle to the outside at the outer circumference edge part of the spherical concave surface 38 of the contact lens 28 is made to be small (close to horizontal, preferably the slant angle downward in relation to a horizontal line is 10 degrees or less). Said another way, with the contact lens 28 arranged at a slant, the distance from the top P2 of the lens loading surface 36 to the outer circumference edge part of the contact lens 28 differs in the circumference direction, and is smallest at each end part positioned at both the left and right sides of the case main unit 10 in FIG. 5.

By doing this, even when oxygen gas (air bubbles) enters the under side of the spherical concave surface 38 of the contact lens 28, for example, by being exhausted relatively easily from the part positioned furthest upward of the outer circumference edge part of the contact lens 28, retention of many air bubbles at the under side of the contact lenses 28 is prevented. As a result, floating up of the contact lens 28 to the liquid surface because of buoyancy due to air bubbles is avoided, and it is possible to effectively maintain a state arranged sufficiently near the lens loading surface 36.

In fact, with this embodiment, at the part for which the outer circumference edge part of the contact lens 28 is positioned the furthest upward, since the gap 46 open to the outer circumference is formed by the groove part 44, based on the guiding action of the air bubbles by this groove part 44, it is possible to more easily allow exhausting of air bubbles to the outside from the under side of the contact lenses 28.

Also, at the catalyst storage portion 18 side, by setting the end edge part of the contact lens 28 to the deepest position, the actual entry of the oxygen gas generated at the perimeter of the catalyst 26 to the under side of the contact lens 28 is also effectively prevented.

In addition, with this embodiment, during the sterilization process, restricting projections 58, 58 of the lid unit 12 enter the lens storage portions 20, 20 of the case main unit 10, and project out into the hydrogen peroxide solution 24, and are positioned above the contact lenses 28, 28 loaded on the lens loading surfaces 36, 36.

By doing this, floating up of the contact lens 28 by oxygen gas entering the under side of the spherical concave surface of the contact lens 28 is prevented to the extent possible, and also, for example even when oxygen gas has entered the under side of the spherical concave surface of the contact lenses 28, the spherical convex surface of the contact lens 28 is pressed from the top side by the restricting projection 58, so floating up to the water surface is prevented. Because of that, across the entire sterilization processing period, a state with the contact lenses 28, 28 completely immersed in the hydrogen peroxide solution 24 is maintained, so it is possible to stably implement the target sterilization process.

Then, by leaving for a designated amount of time, the sterilization process of the contact lenses 28, 28 by the hydrogen peroxide solution 24 is completed. The completion of this sterilization process can be easily confirmed from the fact that the decomposition reaction of the hydrogen peroxide solution 24 is completed by confirming visually that the catalyst 26 has sunk to the bottom of the catalyst storage portion 18. Specifically, the user, after confirming that the decomposition of the hydrogen peroxide solution 24 has completed and has become water, is able to take out the contact lenses 28, 28 which have been sterilized from the solution and safely wear them as is.

Also, there are times when the contact lenses 28, 28 are not worn immediately after completion of neutralization of the hydrogen peroxide solution 24, and in that case, the contact lenses 28, 28 are immersed and stored in liquid for which the sterilization effect has been lost, but even in that state, a holding effect on the sterilized state can be exhibited on the contact lenses 28, 28. Specifically, since the case main unit 10 is formed using an antimicrobial material, the sterilizing action of the case main unit 10 can be efficiently implemented on the contact lens 28 at the lens loading surface 36 which the spherical inner surface of the contact lens 28 is overlapped near or in contact with.

By doing that, it is possible to suppress or prevent the proliferation of microorganisms on contact lenses 28, 28 immersed and stored in the storage solution even after the antimicrobial performance of the storage solution itself has been lost by completion of neutralization of the hydrogen peroxide solution 24, and to keep a safe state avoiding bacterial contamination until the contact lenses 28, 28 are worn by the user. In particular, the contact lens 28 is kept in the storage solution in a state with the lens loading surface 36 that exhibits a sterilizing action overlapped directly on the spherical concave surface 38 of the contact lens 28 for which adverse effects of microorganisms easily become a problem when wearing the contact lens 28. Thus, it is possible to more effectively exhibit the sterilizing action on the contact lens 28. In particular, by forming the entire case main unit 10 using a bactericidal resin or the like so as to give antimicrobial properties in a wide range of the case inner surface area contacted by the storage solution, it is possible to obtain even better antimicrobial performance. It is also possible to form the lid unit 12 using a bactericidal resin as well, but for example by forming the lid unit 12 with a high transparency material, it is also possible to make it possible to visually recognize from outside the case the state of the contact lens or storage solution being sterilized without removing the lid unit 12.

Furthermore, the lens loading surface 36 is a spherical shape that is convex upward, and since the contact lens 28 is supported in a state loaded overlapping the spherical concave surface there, when wearing the contact lens 28, the user inserts a finger in the storage solution from the opening part of the lens storage portion 20 that appears by removing the lid unit 12 to have an open state, and it is possible to pull it out in a state with the spherical convex surface of the contact lens 28 overlapping the round part of the finger tip. By doing this, the user is able to take out the contact lens 28 from the contact lens case 14 and put it on the cornea without touching the finger to the contact lens 28 on the spherical concave surface 38 side for which microbial contamination easily becomes a problem.

Also, with this embodiment, by the catalyst 26 undergoing sinking-floating along with progression of the decomposition reaction of the hydrogen peroxide solution 24, a stirring and flow action are implemented on the hydrogen peroxide solution 24. In particular with this embodiment, cutout windows 32, 32 that reach from the bottom edge to the top edge are formed on the partition walls 30, 30 with the catalyst storage portion 18 and the lens storage portions 20, 20 providing a communication flow path. Therefore, even with oxygen gas air bubbles generated in the perimeter of the catalyst 26 that float up and further diffuse to the periphery near the water surface, the stirring and flow action are implemented on the hydrogen peroxide solution 24. In addition, between the bottom surfaces of the lens storage portions 20, 20 and the catalyst storage portion 18, by setting the heights differently (slant or step), using the difference in specific gravity between the hydrogen peroxide solution 24 and water after its decomposition, the undecomposed hydrogen peroxide solution 24 is actively led from the lens storage portions 20, 20 toward the catalyst storage portion 18, and by being collected near the catalyst 26, it is possible to more safely and efficiently exhibit the catalytic action.

In this way, with the contact lens case 14 of this embodiment, by actively implementing a flow action on the hydrogen peroxide solution 24 within the liquid holding recess 16 including the catalyst storage portion 18 and the lens storage portions 20, 20, it is possible to homogenize the decomposition reaction of the hydrogen peroxide solution 24. As a result, the target sterilization process of the contact lens 28 can be performed stably over a roughly constant time with the concentration of the hydrogen peroxide solution 24 controlled with good precision.

Above, we gave a detailed description of one embodiment of the present invention, but the present invention is not to be interpreted as being limited by the specific notations of this embodiment, and various types of modifications and revisions can be added based on the knowledge of a person skilled in the art.

For example, the present invention can also be used for a contact lens case used with the MPS method that uses MPS fluid instead of the previously described hydrogen peroxide solution 24 as the storage solution with a sterilizing action. In that case, since the catalyst is unnecessary, it is also not necessary to provide the catalyst storage portion in the case main unit, and for example it is possible to use a constitution equipped with only a pair of lens storage portions that are in communication with each other or that are independent and not in communication.

Then, by using the present invention on that kind of contact lens case used for the MPS method as well, by the weak sterilizing action with the MPS solution being supplemented by the sterilizing action of the lens case itself, by the sterilizing action of the solution and the lens case working in cooperation, it is possible to give an excellent sterilizing effect to the contact lens immersed in the MPS solution. In particular, by the sterilizing action of the lens case being actively implemented on the spherical concave surface of the contact lens for which adverse effects due to adherence of microorganism easily become a problem, the same effect as the previously described embodiment such as being able to efficiently avoid problems due to adherence of microorganisms can be exhibited in the same way with the MPS method.

In fact, when the contact lens is immersed in the MPS solution and overlapped on the lens loading surface, or when after the contact lens is loaded on the lens loading surface the MPS solution is inserted in the lens storage portion, for example even when air bubbles enter the under side of the contact lens, those air bubbles are easily exhausted from the outer circumference edge part of the topmost part of the contact lens held in a slanted state, preventing the remaining of a large amount of air bubbles on the under side of the contact lens. Because of that, the same as with the previously noted embodiment showing an application example to the hydrogen peroxide solution method, by the spherical inner surface of the contact lens being effectively overlapped in a state near the lens loading surface, it is possible to have the sterilizing action of the lens loading surface on the contact lens exhibited stably and effectively.

Also, in the case of a contact lens case used for either of the MPS method or the hydrogen peroxide method, it is not absolutely necessary to have the partition walls 30, 30 provided between the catalyst storage portion 18 and the lens storage portions 20, 20. Of course, in the case of a contact lens case used for the hydrogen peroxide method, with the goal of avoiding the adverse effect of metal ions or the like of the catalyst 26, it is desirable to provide means for avoiding contact of the contact lens 28 on the catalyst 26, for example, by inputting the catalyst 26 in a basket, or restricting the movement of the contact lens 28 by a regulating projection or the like. Also, with the goal of promoting the neutralization reaction of the hydrogen peroxide solution 24, it is possible to use a known neutralization accelerant or the like instead of the metal catalyst, and in that case, it is not necessary to provide the partition wall 30 or the like for partitioning the lens storage portions 20, 20 and the catalyst storage portion 18.

Furthermore, in a case when the partition wall is provided as well, this is not particularly limited to being an item of a specific shape or constitution for the partition wall itself, and there is no particular limit on the specific constitution or number or the like of the communication flow paths that connect the catalyst storage portion 18 and the lens storage portions 20, 20 formed on the partition wall. For example, it is possible to constitute the communication flow path by forming a partition wall that partitions across the entire catalyst storage portion 18 and the lens storage portions 20, 20 as well as having a suitable number of through holes provided on that partition wall.

Also, the specific shape of the lens support part 34 and the lens loading surface 36 is not limited to the previously noted embodiment. For example, as with the contact lens case 60 which is a second embodiment of the present invention shown in FIG. 6, it is also possible to have a mode for which the entire surface of the spherical concave surface of the contact lens 28 is positioned facing opposite and roughly uniformly near the lens loading surface 36 without providing a groove part (44) on the lens loading surface 36. With the contact lens case 60 of FIG. 6, at the bottom surface of the catalyst storage portion 18, a slope slanting gradually downward is added overall facing from both side end parts at left and right toward the center part, and by adding a slope continuously from the slant of the bottom surface 42 of each circumferential groove 40 of the lens storage portions 20 of both sides, the hydrogen peroxide solution 24 is made to be more efficiently collected at the catalyst storage portion 18 from both sides of lens storage portions 20, 20 using specific gravity.

Figure 6:
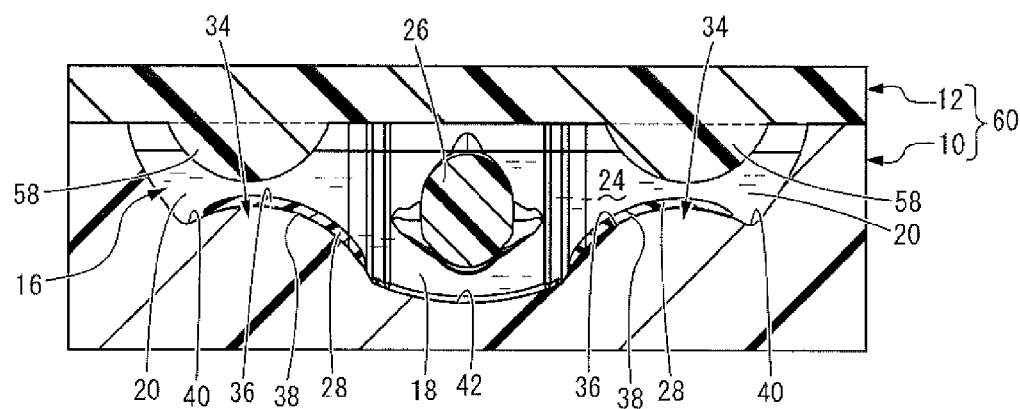
FIG. 6 is a cross section view correlating to FIG. 5 showing a contact lens case as a second embodiment of the present invention.

Furthermore, by making the curvature radius of the lens loading surface 36 shown in FIG. 6 different according to the area, by having the lens loading surface 36 be an elliptical shape, it is possible to actively form a gap that opens to the outer circumference side of the contact lens 28 between the lens loading surface 36 and the contact lens 28. In specific terms (though not illustrated in the drawings), by forming an elliptical shaped lens loading surface 36 that broadens in the front-back direction with a front view by making the curvature radius on the diameter extending in the left-right direction of the case main unit 10 (left-right direction in FIG. 1) smaller than the curvature radius on the diameter extending in the front-back direction (vertical direction in FIG. 1), it is possible to form a gap opened at the outer circumference edge part of the topmost part of the contact lens 28 loaded on the lens loading surface 36.

Figure 7:
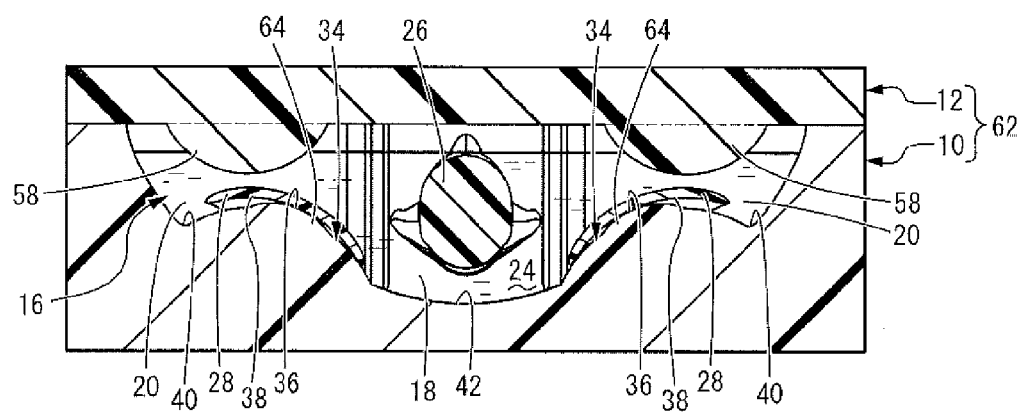
FIG. 7 is a cross section view correlating to FIG. 5 showing a contact lens case as a third embodiment of the present invention.

Alternatively, as with the contact lens case 62 which is a third embodiment of the present invention shown in FIG. 7, at the center part of the lens loading surface 36, it is also possible to form a circular area smaller than the contact lens 28 projecting out with a spherical convex surface 64 with a curvature radius smaller than that of the spherical concave surface of the contact lens 28. By supporting the center part of the spherical concave surface of the contact lens 28 on this spherical convex surface 64, it is possible to actively form a gap 46 that opens at the outer circumference edge part of the topmost part of the contact lens 28 supported in a slanted state.

Keys to Symbols

10: Case main unit, 12: Lid unit, 14, 60, 62: Contact lens case, 16: Liquid holding recess, 18: Catalyst storage portion, 20: Lens storage portion, 24: Hydrogen peroxide solution, 26: Catalyst, 28: Contact lens, 30: Partition wall, 32: Cutout window (communication flow path), 34: Lens support part, 36: Lens loading surface, 38: Spherical concave surface, 40: Circumferential groove, 42: Bottom surface, 44: Groove part, 46: Gap, 48: Support projection, 50: Catalyst main unit, 52: Frame unit, 54: Support shaft, 56: Engaging piece, 58: Restricting projection, 64: Spherical convex surface

The invention claimed is:

1. A contact lens case that is used repeatedly for sterilizing a contact lens with a storage solution with a sterilizing action, comprising:
    a lens storage portion opening upward for storing the contact lens with the contact lens being immersed in the storage solution with the sterilizing action; and
    a lens loading surface is provided projecting at a bottom part of the lens storage portion so as to have a curved shape that is convex upward and be positioned under a liquid surface of the storage solution,
    wherein:
    the lens loading surface is adapted to hold the contact lens placed on the lens loading surface with a spherical concave surface of the contact lens overlapping the lens loading surface,
    the lens loading surface is formed by an antimicrobial material,
    the lens loading surface has a geometric center that is set at a position separated downward from a top of the lens loading surface so that the contact lens rests on the lens loading surface with the geometric center being positioned separate from the top of the lens loading surface, and
    a curvature radius of the lens loading surface is smaller than a curvature radius of an inner surface of the contact lens, and an upper side part of the lens loading surface has a smaller curvature radius than a lower side part of the lens loading surface so that a gap is formed between the lens loading surface and the inner surface of an outer circumference edge part of the contact lens, at the upper side part of the lens loading surface in order to avoid retention of air bubbles generated in sterilization under a bottom side of the contact lens.

2. The contact lens case according to claim 1, wherein a height position of an outer circumference edge part of the lens loading surface is different in a circumferential direction so that the geometric center of the lens loading surface is set at a position separated from the top, and the outer circumference edge part of the lens loading surface is adapted to regulate a position of the outer circumference edge part of the contact lens.

3. The contact lens case according to claim 1, wherein on the lens loading surface, a groove part extending in a radial direction is formed with a side facing opposite a side for which the geometric center of the lens loading surface is separated from the top of the lens loading surface.

4. The contact lens case according to claim 1, wherein across an entire surface of an area on which the contact lens is loaded on the lens loading surface, a curvature radius of the lens loading surface is smaller than a curvature radius of an inner surface of the contact lens.

5. The contact lens case according to claim 1, wherein hydrogen peroxide solution is held as the storage solution in the lens storage portion.

6. The contact lens case according to claim 5, further comprising a catalyst storage portion that holds a catalyst exhibiting a catalytic action on a decomposition reaction of the hydrogen peroxide solution with a bottom surface of the catalyst storage portion being located at a same or greater depth as a bottom surface of the lens storage portion, and a bottom part communication flow path that causes communication between the lens storage portion and the catalyst storage portion at the bottom part.

7. The contact lens case according to claim 5, wherein a catalyst exhibiting a catalytic action on a decomposition reaction of the hydrogen peroxide solution is used, and the catalyst includes a catalyst main unit and a frame unit enclosing an outer circumference of the catalyst main unit.

8. The contact lens case according to claim 1, further comprising a lid unit that closes the lens storage portion being provided to be able to open and close, and a restricting projection that restricts floating up of the contact lens from the lens loading surface being provided on an inner surface of the lid unit so as to be positioned facing the lens loading surface of the lens storage portion and project as far as the storage solution.

\* \* \* \* \*